United States Patent [19]

Chubbuck et al.

[11] Patent Number: 4,627,443

[45] Date of Patent: Dec. 9, 1986

[54] X-RAY READABLE IMPLANTABLE PRESSURE SENSOR

[75] Inventors: John G. Chubbuck, Silver Spring; Melvin H. Epstein, Glyndon, both of Md.

[73] Assignee: The Johns Hopkins University, Baltimore, Md.

[21] Appl. No.: 201,757

[22] Filed: Oct. 29, 1980

[51] Int. Cl.$^4$ ............................................. D61B 5/00
[52] U.S. Cl. ................................... 128/748; 128/1 R
[58] Field of Search ............... 128/632, 637, 653, 654, 128/659, 673, 674, 675, 748, 1 R

[56] References Cited

U.S. PATENT DOCUMENTS

| 4,006,735 | 2/1977 | Hittmann et al. | 128/748 |
| 4,022,190 | 5/1977 | Meyer | 128/748 |
| 4,172,449 | 10/1979 | Leroy et al. | 128/748 |
| 4,186,751 | 2/1980 | Fleischmann | 128/748 |

Primary Examiner—William E. Kamm
Attorney, Agent, or Firm—Robert E. Archibald; Howard W. Califano

[57] ABSTRACT

A pressure sensor for measuring pressure of a body at a selected site is provided wherein radiopaque means shift in response to pressure. The body is X-rayed using conventional techniques and the shifting of the radiopaque means is observed to indicate the change in pressure. Several embodiments of the present invention are suited for biomedical applications.

10 Claims, 10 Drawing Figures

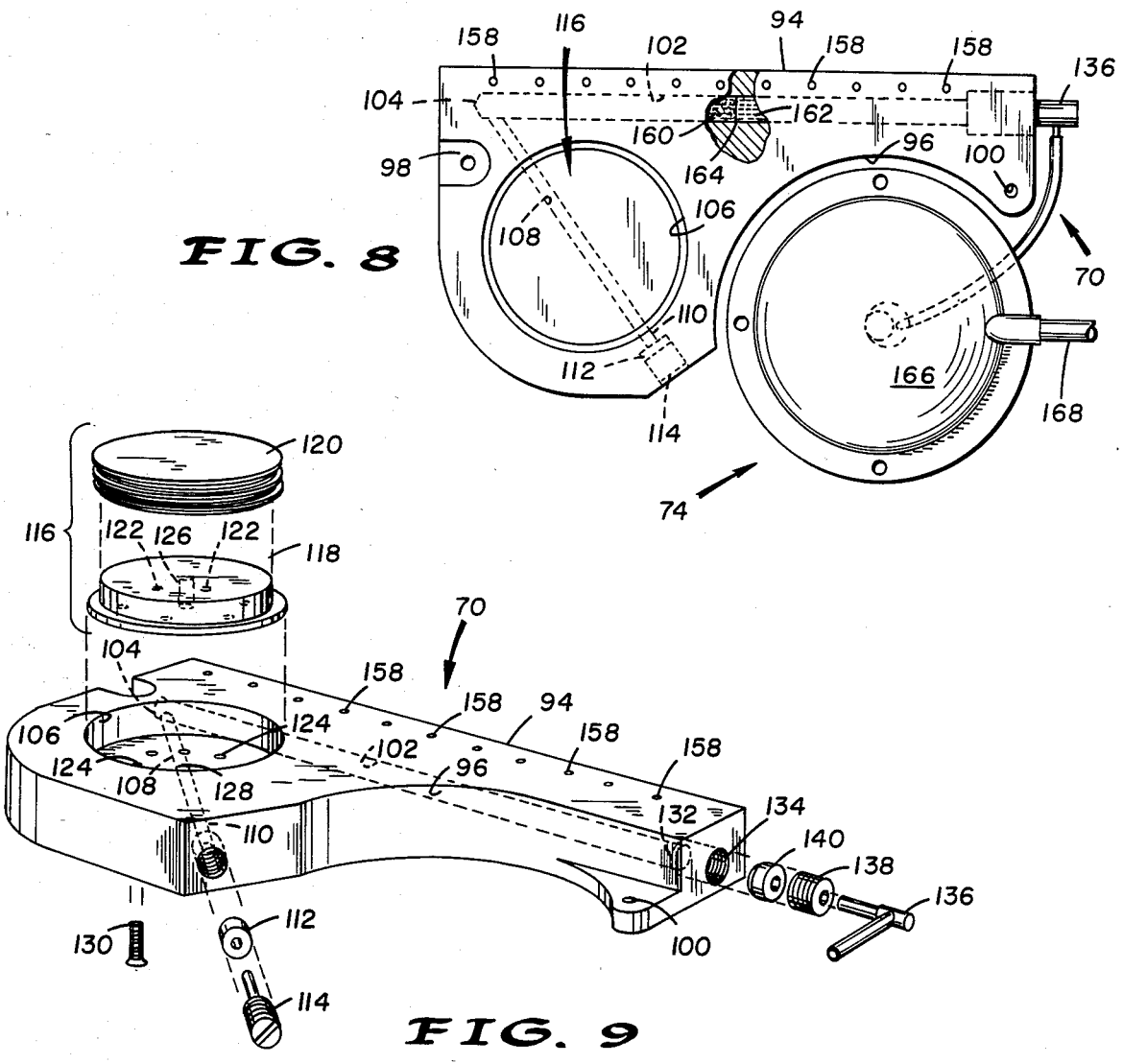
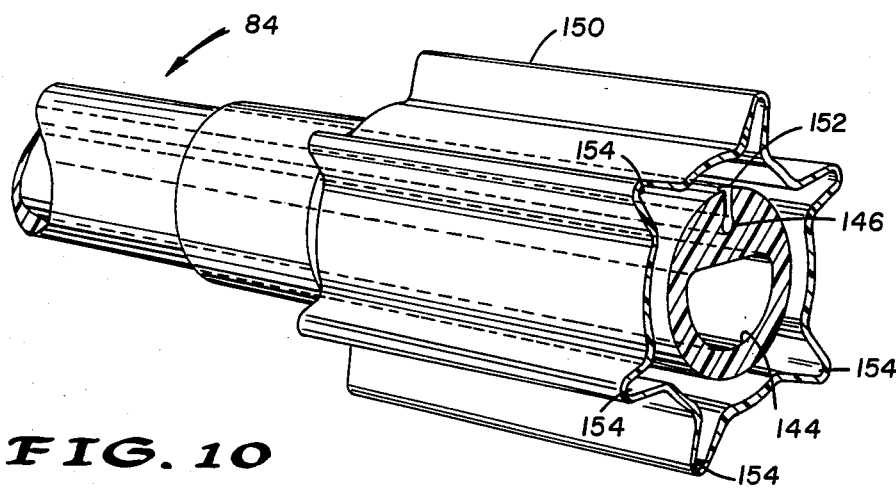

X-RAY READABLE IMPLANTABLE PRESSURE SENSOR

STATEMENT OF GOVERNMENTAL INTEREST

The Government has rights in this invention pursuant to Research Grant Nos. NS07226 and NS13610 from the Department of Health and Human Services.

BACKGROUND AND/OR ENVIRONMENT OF THE INVENTION

1. Field of the invention

The present invention relates to pressure sensors for measuring body pressure at a selected site, and more particularly to an implantable pressure sensor which can be interrogated by X-ray of the body in which it is implanted to observe changes in pressure therein.

2. Description of the contemporary and/or prior art

There are several situations where the monitoring of pressure is necessary. In some of these situations, particularly in the biomedical arts, it is desirable to have a device which is entirely implantable within a body. For instance, it is frequently desirable to monitor ventricular pressure in hydrocephalics so that cerebrospinal fluid (CSF) can be drained from the ventricle if necessary or appropriate, or so that drug therapy can be initiated. Many prior art devices have been proposed which are transcutaneous, i.e., a portion thereof extends through the scalp of the patient to an appropriate readout device. The major drawback of these devices is the chance of infection at the site where the device breaches the scalp and the severe limitation on mobility of the patient.

Others in the art have sought to avoid this problem by using various fully implantable electronic devices which are interrogated by induction or which transmit coded information to an appropriate monitor. Aside from the requirement of having complex precision electronic equipment which must be implanted inside the head of a patient and the attendant cost, sophisticated monitoring apparatuses must also be employed. In addition, many of these apparatuses measure pressure across the dura rather than in the ventricle, a pressure, which in many medical circles, is not considered to be the same as ventricular pressure.

The treatment of hydrocephalus frequently involves implantation of a ventricular shunt and flushing valve arrangement for draining cerebrospinal fluid. None of the apparatuses presently known for monitoring and providing a readout of pressure are configured to be integratable with presently known shunt and flushing valve arrangements.

Of some of the known pressure monitoring devices, U.S. Pat. Nos. 3,977,391 and 4,124,023 issued to Fleischmann et al, and U.S. Pat. No. 4,006,735 issued to Hittman et al teach pressure sensing apparatuses wherein a tambour is exposed to pressure and a fluid in the tambour is forced thereout. In these apparatuses, this moving fluid is used to shift radioactive material relative to a shield in proportion to pressure changes so that the quantity of radioactive material can be statistically analyzed to determine relative pressure. While these configurations avoid the necessity of implanting electronics in the patient, a sophisticated monitoring apparatus is still needed to determine the amount of observed radioactivity.

Other pressure monitors which employ a sac or bladder filled with a fluid which is subjected to pressure include U.S. Pat. No. 3,911,902 issued to Delpy and U.S. Pat. No. 2,566,369 issued to Putman. These references teach the forcing of fluid through a calibrated tube so that pressure can be read by direct observation. Alternately, in Putnam, electrodes can be placed in the tube to determine position of the fluid. In Delpy, a liquid/gas interface shifts in a capillary tube thereby varying the capacitance between two wires disposed in the tube. By detecting changes in capacitance, a relative pressure can be indicated. Unfortunately, these apparatuses cannot be totally implanted and either the pressure readout scale or the wires of these apparatus must be transcutaneously positioned for readout. Therefore, the previously mentioned problems of immobility and infection exist.

The present invention overcomes the problems associated with the prior art by providing a totally implantable pressure sensor for measuring body pressure at a selected site within the body wherein a radiopaque material is mechanically shifted in proportion to changes in pressure. The subject or patient can then be X-rayed on widely available X-ray machines using known techniques to determine changes of pressure. This avoids the necessity of complex monitoring apparatuses or the use of transcutaneous configurations which not only subject the patient to a great risk of infection but also severely limit the mobility of the patient and therefore the possibility of long term pressure monitoring.

In several embodiments of the present invention this is accomplished through the use of a radiopaque fluid which shifts in position. Radiopaque fluids are known for use in variable pressure valves and are shown in U.S. Pat. Nos. 3,886,948 and 3,924,635 issued to Hakim. However, the radiopaque fluids in these apparatuses are used primarily for dampening and so that the position of the pressure sensing bladder of these devices can be determined by X-ray. Interrogating the relative position of the radiopaque fluid to determine changes in pressure are not shown or suggested and these devices merely use the shifting of the radiopaque fluid to trigger mechanical structure to perform the desired function.

In a further advance over the art, the present invention teaches the integration of a pressure monitoring device with a ventricular shunt. In a vaguely similar manner, U.S. Pat. No. 4,214,593 to Imbruce et al teaches an esophagal pressure device wherein a multiple lumen tube is employed, one of the lumens communicating with a balloon cup filled with a gas, the other lumen being used for typical nasogastric applications. As pressure acts on the balloon cuff, the gas is passed through the associated lumen so that changes in pressure can be monitored by an external monitor. This device is basically for transitory use and implantation is not shown or suggested.

Shifting of radiopaque material in a pressure monitor is shown in U.S. Pat. No. 4,172,449 issued to LeRoy et al. LeRoy teaches a body fluid pressure monitor wherein a radiopaque fluid disposed in a chamber distends the wall of the chamber, the curvature of the wall of the chamber showing relative changes in pressure. In another embodiment several radiopaque dots disposed on the outer surface of a balloon shift relative to each other as the balloon expands. Additionally, a Bourdon tube arrangement wherein a radiopaque marker shifts in response to pressure is also shown. Unfortunately, none of these configurations can supply precisely readable indications of pressure changes since the curvature of a membrane or the separation of radiopaque material in a non-linear manner is not easily calibratable when the angle at which the radiopaque material will be X-rayed cannot be exactly repeated. The present invention provides significant advantages over these configurations through the use of readily calibratable movement of radiopaque material which can read out giving direct quantitive indications of pressure changes.

SUMMARY OF THE INVENTION

Therefore, a primary object of the present invention is to provide a pressure sensor which is totally implantable within a body and which can be interrogated to observe changes in pressure through the use of X-rays.

A further object of the present invention is to provide a pressure sensor ideally suited for implantation in a human body.

A still further object of the present invention is to provide a pressure sensor which can be interrogated through commonly available X-ray procedures using presently available equipment, thereby obviating the need for sophisticated, specialized and presently not immediately available monitoring equipment.

Still another object of the present invention is to provide a pressure sensor which is compact in design and is therefore suitable for positioning in small areas.

Still another further object of the present invention is to provide an X-ray readable, implantable pressure sensor for monitoring ventricular pressure which is readily integratable with a ventricular shunt.

Another further object of the present invention is to provide an X-ray readable, implantable pressure sensor which can be contoured to conform to the shape of a ventricular pressure shunt to facilitate implantation of the pressure sensor and the shunt simultaneously, as a combined compact unit.

Still another object of the present invention is to provide an X-ray readable, implantable pressure sensor which is passive and therefore does not need any power source.

Another still further object of the present invention is to provide an implantable, X-ray readable pressure sensor which is of the differential type so that the change in pressure being monitored is automatically corrected with respect to changes of atmospheric pressure.

An additional object of the present invention is to provide a pressure sensor which is suitable for long term implantation.

A still additional object of the present invention is to provide a biomedical pressure sensor which can be implanted using, and as an adjunct to, known surgical techniques and procedures.

Still another additional object of the present invention is to provide a pressure sensor which is simple in design, relatively inexpensive to manufacture, rugged in construction, relatively simple to implant, readily readable, and efficient in operation.

These objects as well as further objects and advantages of the present invention will become readily apparant when reading the ensuing description of several non limiting illustrative embodiments and the accompanying drawings.

A pressure sensor for measuring body pressure at a selected site within the body, according to the principles of the present invention, comprises a movable X-ray detectable radiopaque means; and means for translating changes in the pressure to movement, the movement moving the movable radiopaque means, the relative positioning of the radiopaque means being determinable by X-raying of the body.

BRIEF DESCRIPTION OF THE DRAWINGS

In order that the present invention may be more fully understood, it will now be described by way of example, with reference to the accompanying drawings in which:

FIG. 8 is a top plan view of the embodiment illustrated in FIG. 7;

FIG. 9 is an exploded view in perspective of the embodiment illustrated in FIGS. 6, 7 and 8; and FIG. 10 is a cross sectional view in perspective of the tambour and ventricular shunt of the present invention.

DESCRIPTION OF THE PREFERRED EMBODIMENTS

Figure 1:
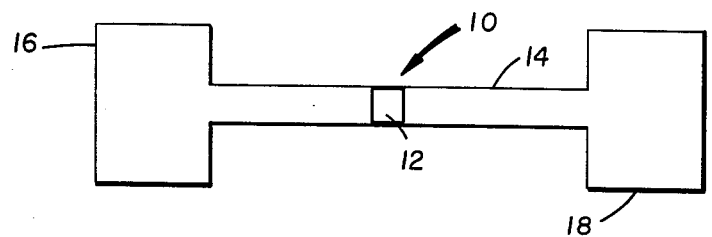
FIG. 1 is a schematic representation of one embodiment of the present invention.

Referring now to the figures, and more particularly to FIG. 1, there is illustrated therein a schematic representation of a pressure sensor incorporating the principles of the present invention therein. The sensor 10 includes a movable X-ray detectable means 12. The movable X-ray detectable means 12 is disposed in a conduit 14 connected on one end thereof to a first variable volume means 16 and on the other end thereof to a second variable volume means 18. The sensor 10 would be employed with the first variable volume means 16 disposed at the site where the pressure change is to be monitored. If the invention is to be used in a differential mode, the second variable volume means 18 would be exposed to a second pressure. For instance, the first variable volume means 16 might be implanted in a human brain ventricle, and the second variable volume means 18 might be exposed to atmospheric pressure so that ventricular pressure could be measured discounting changes in atmospheric pressure. Alternately, the first variable volume means 16 could be disposed at one site in an apparatus and the second variable volume means 18 could be disposed at another site to read the differential pressure therebetween.

The change in volume of the variable volume means 16 is employed to shift the position of the movable X-ray detectable means 12 within the conduit 14. This can be accomplished in many ways all within the scope of the present invention. For instance, the variable volume means 16 and the adjacent portion of the conduit 14 can be filled with a liquid, the X-ray detectable means 12 can make a sliding seal with the conduit 14, and the balance of the conduit 14 adjacent to the second variable volume means 18 can also be filled with a liquid. If the first variable volume means has flexible walls, for instance if it is a tambour, and the second variable volume means 18 also has flexible walls, for instance, if it too is a tambour or if it is a closed ended bellows, when pressure impinges on the variable volume means 16 the fluid disposed therein will shift thereout pushing the X-ray detectable means 12 through the conduit 14, which in turn will shift the fluid on the other side of the X-ray detectable means 12 with the variable volume means therefore 18 expanding. Alternately, the second variable volume means 18 can be rigid walled, and filled with a gas. As the liquid in the first variable volume means 16 shifts to move the X-ray detectable means 12 through the conduit 14, this will compress the gas and the effective volume of the second variable volume means will decrease as a result. Of course, the last mentioned configuration would operate as a reference pressure sensor, the gas serving as the reference pressure, rather than as a differential pressure sensor.

Alternatively, in a configuration which is employed in the embodiments illustrated in FIGS. 2 through 10, the first variable volume means 16 is flexible walled, for instance a tambour, and the second variable volume means 18 is also flexible walled, for instance a closed ended bellows. The first variable volume means 16 is filled with a liquid, for instance, saline solution (not illustrated) and, rather than employing the X-ray detectable means 12 which is a discrete element, a radiopaque liquid (not illustrated) is employed which fills the balance of the conduit 14 not filled by the saline solution, and the second variable volume means 18. The interface between the saline and the radiopaque means shifts as pressure is experienced at the first variable volume means 16 or tambour. This shifts the radiopaque liquid in the conduit 14 and forces the same into the second variable volume means thereby moving the interface between the radiopaque liquid and the saline along the conduit 14. If the conduit 14 is calibrated with markings, changes in pressure can readily be ascertained by X-raying the body in which the sensor 10 is implanted.

It should also be apparent to one of ordinary skill in the art that mechanical rather than hydraulic coupling can be employed in the present invention and, for instance, a radiopaque material can be affixed to a membrane which flexes in response to pressure, the relative position of the membrane indicating the change in pressure.

Figure 2:
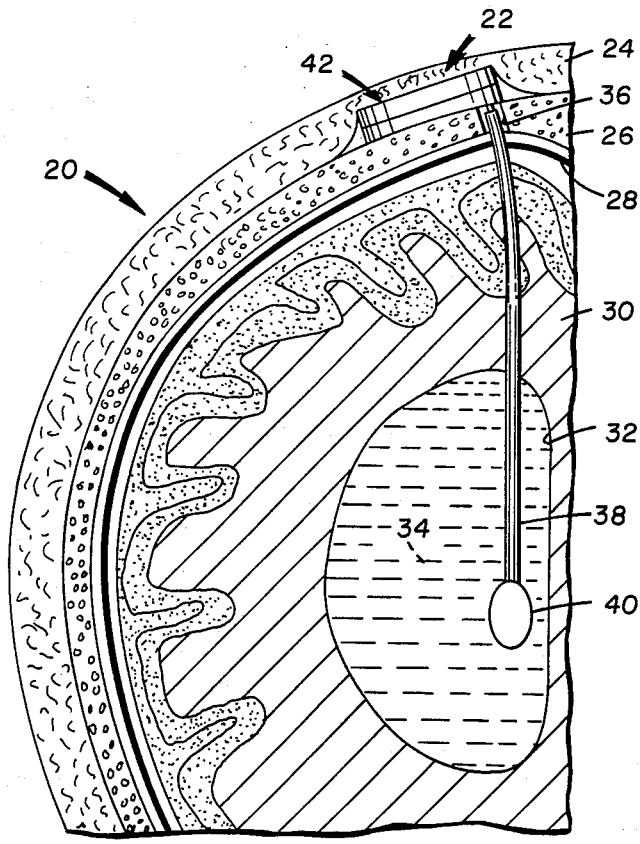
FIG. 2 is a pictorial representation of the present invention mounted on a cranium for measuring the ventricular pressure within the brain disposed therein.

With the general teachings of the present invention now in mind, it is beneficial to look at two specific embodiments where the present invention has been employed in biomedical applications. However, it is to be understood that these principles and teachings may be employed in other than biomedical applications. With reference to FIG. 2, there is illustrated therein a head 20 in which a pressure sensor 22, incorporating the principles of the present invention, has been implanted. The head 20 includes scalp 24, a cranium 26, dura 28, brain tissue 30 and a brain ventricle 32 filled with cerebrospinal fluid (CSF) 34.

The sensor 22 is shown affixed to the cranium 26. This is accomplished by known techniques such as suturing. An aperture 36 has been formed in the cranium 26 to permit passage of a pressure tube 38 through the cranium 26. The pressure tube 38 also passes through the dura 28 and the brain tissue 30 into the ventricle 32. A tambour 40 is operably disposed at the end of the pressure tube 38 as hereinafter described to measure pressure changes in the CSF 34. The sensor 22 includes a housing 42 which contains the balance of the device.

Figure 3:
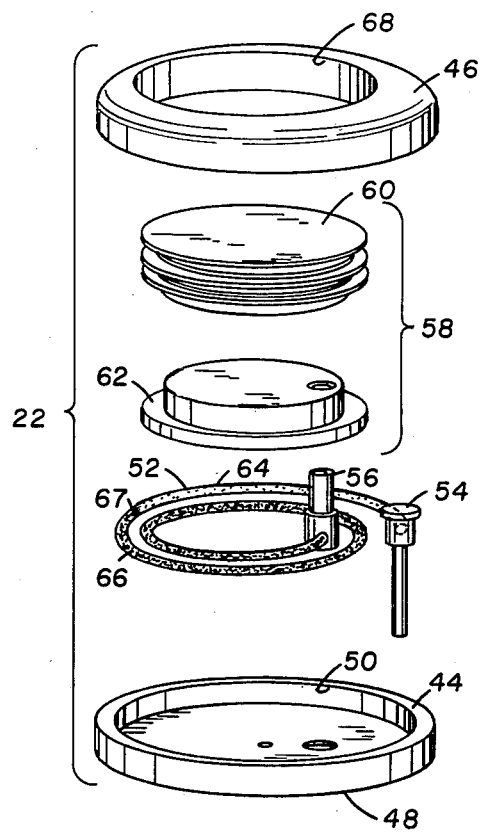
FIG. 3 is an exploded view in perspective of the embodiment of the present invention shown in FIG. 2.
Figure 4:
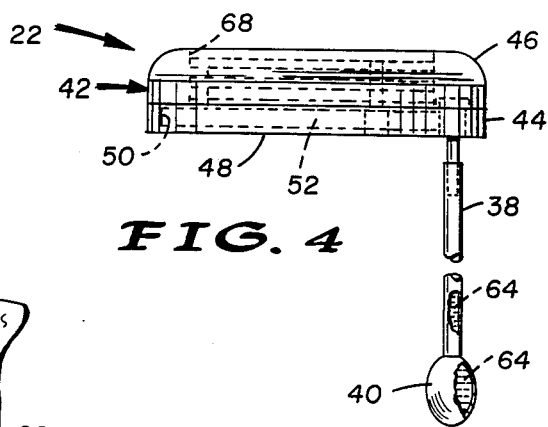
FIG. 4 is a side view of the assembled embodiment of FIG. 3.
Figure 5:
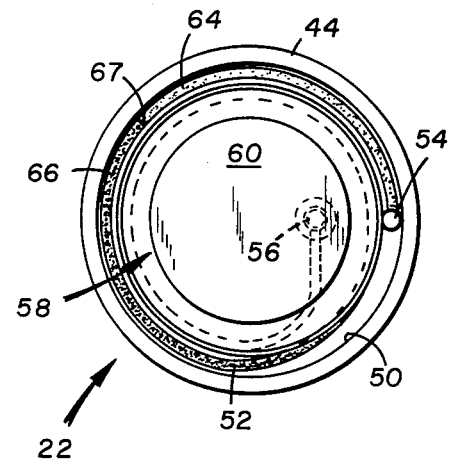
FIG. 5 is a top view of the assembled embodiment of FIG. 3.

A better understanding of this embodiment can be ascertained by viewing FIGS. 3, 4 and 5. The housing 42 of the sensor 22, as illustrated in FIG. 4, includes a lower housing plate 44 and an upper housing portion 46 which are dimensioned to be assembled employing suitable means for joining these elements together as illustrated in FIG. 4.

The lower housing plate 44 is configured on the lowermost surface 48 thereof to rest on the cranium 26 as illustrated in FIG. 2. Furthermore, the lowermost housing plate 44 has disposed therein a recess 50 for accommodating a flat coil of tubing 52. The coil of tubing 52 has a coupling 54 disposed on the outer end thereof and a coupling 56 disposed on the inner end thereof. The interior of the tubing 52 is connected to the interior of the pressure tube 38 through the coupling 54, the tube 38 being inserted over a portion of the coupling 54 as illustrated in FIGS. 2 and 4.

The other end of the pressure tube 38 has disposed thereon the tambour 40, the interior of the tambour being in communication with the interior of the pressure tube 38. The inner end of the flat coil of tubing 52 is connected by the coupling 56 to a closed ended bellows assembly 58 which comprises a bellows member 60 and a bellows closure plate 62. The bellows member 60 is fixedly secured to the bellows closure plate 62 creating an hermetic seal and forming a chamber therebetween. The coupling 56 is secured to the bellows plate 62 so that the interior chamber of the bellows assembly 58 is in communication with the flat coil of the tubing 52. When assembled as illustrated in FIG. 54, the tambour 40, pressure tube 38, flat coil of tubing 52, and closed ended bellows assembly 58 comprise a sealed unit, the interior of which is not in communication with the environment.

The interior of the tambour 40, the pressure tube 38, and the adjacent portion of the flat coil of tubing 52 is filled with a liquid 64 such as saline or the like. The balance of the interior of the flat coil of tubing 52 and the entire interior chamber of the closed ended bellows assembly 58 is filled with a radiopaque liquid 66. The saline 64 is immiscible in the radiopaque liquid 66 and an interface or meniscus 67 is formed therebetween. As illustrated in FIG. 5, the diameter of the closed ended bellows assembly 58 is such that it is smaller than the flat coil of tubing 52 so that approximately 300° of the outermost coil of the tubing 52 is visible when the sensor 22 is viewed from above. The interface 67 between the liquids 64 and 66 shifts through this exposed area to indicate changes in pressure.

The upper housing portion 46 has an opening 68 disposed therethrough to accommodate reciprocation of the bellows member 60 therein. The bellows member 16, at maximum deflection, is no higher than the top surface of the upper housing portion 46 so it does not protrude therefrom. As a result, tissue pressure of the scalp 24 does not impinge on the closed ended bellows assembly 58. However, the scalp 22 acts as an excellent transfer agent for atmospheric pressure to the closed ended bellows assembly 58. Therefore, when the sensor 22 is implanted as illustrated in FIG. 2, it will work in a differential mode, automatically correcting the readings of ventricular pressure for changes in atmospheric pressure.

In use, as pressure increases in the ventricle 32, it acts upon the tambour 40 to diminish the volume thereof.

This forces saline 64 up through the pressure tube 38 and causes the radiopaque liquid 66 to also shift within the flat coil of tubing 52. As a result of this shift, the interface 67 between these liquids shifts in a counterclockwise direction as viewed in FIG. 5, and the radiopaque fluid 66 is forced into the interior of the closed ended bellows assembly 58. If a decrease in pressure takes place in the ventricle 32, the opposite effect will happen and the interface 67 between the saline 64 and the radiopaque liquid 66 will move in the opposite direction, in this instance clockwise when the apparatus is observed as illustrated in FIG. 5.

It should be apparent that the present invention can be readily read out or interrogated with the use of a conventional X-ray technique to determine the position of the interface 67 between the radiopaque liquid 66 and saline 64.

If desired, a plurality of radiopaque markers can be positioned within the housing 42, separated distances corresponding to specific changes in pressure, along the tubing 52. This facilitates interpretation of the pressure readings obtained by X-ray. Alternately, the coil of tubing 52 can be calibrated so certain changes in the radial position of the interface can be interpreted to mean predetermined changes in pressure. Obviously, the coil of tubing 52 can be configured other than in a coil as desired.

The elements of sensor 22 can be readily constructed of well-known biologically compatible materials. The diameter of the flat coil of tubing 52 must be such that shift of the radiopaque fluid over the saline or vice versa does not occur. This can be readily determined by one skilled in the art when the properties of the chosen fluids are known. In an embodiment constructed, Pantopaque radiopaque fluid, a product of Lafayette Pharmaceuticals, Inc., used in a coil having an inner diameter of 0.85 millimeters proved satisfactory. Another consideration is minimizing adhesion between the radiopaque liquid and the interior surface of the tubing 52. Teflon, a synthetic resin polymer product of Dupont appears to be most desirable for this application.

Figure 6:
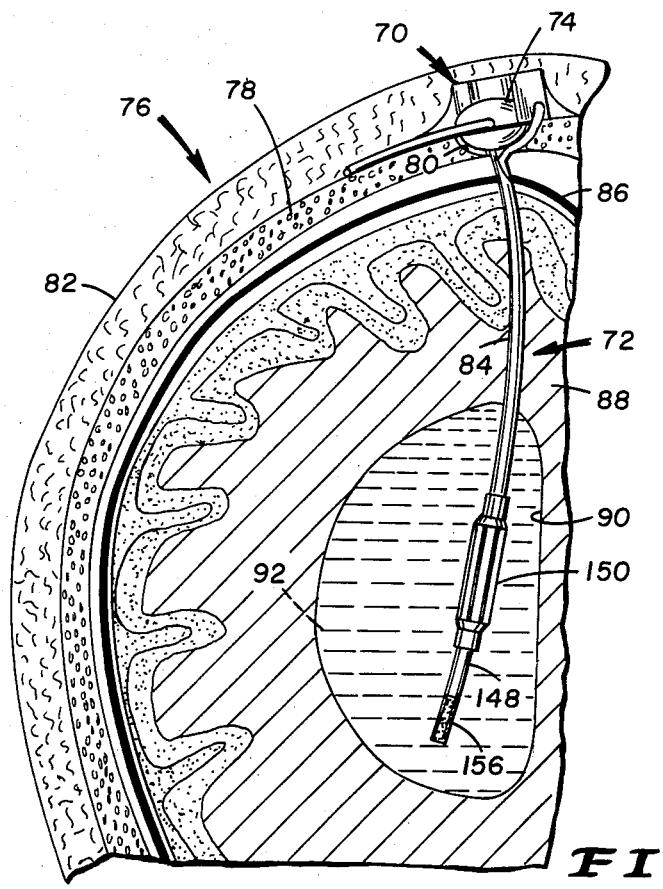
FIG. 6 is a pictorial representation of another embodiment of the present invention in position for measuring ventricular pressure within the brain.

FIG. 6 shows an alternate embodiment of the present invention, a pressure sensor 70. The pressure sensor 70 is configured for use in conjunction with a ventricular pressure shunt 72 and an associated flushing valve 74 all surgically implanted in a head 76. The pressure sensor 70 and the ventricular shunt 74 are mounted to the cranium 78 of the head 76. An aperture 80 is disposed in the cranium 78 to accommodate a portion of the flushing valve 74 and a portion of the pressure sensor 70 as hereinafter described. The pressure sensor 70 and ventricular shunt 72 are covered by the scalp 82 of the head 76. A double lumen tube 84, which serves as part of the ventricular shunt 72 and part of the pressure sensor 70, extends through the aperture 80, the dura 86 and the brain tissue 88, into the ventricle 90 thereof. The ventricle 90 is filled with CSF 92, the pressure of which is measured by the sensor 70, the CSF being drained through the ventricular shunt 72 as desired.

Figure 7:
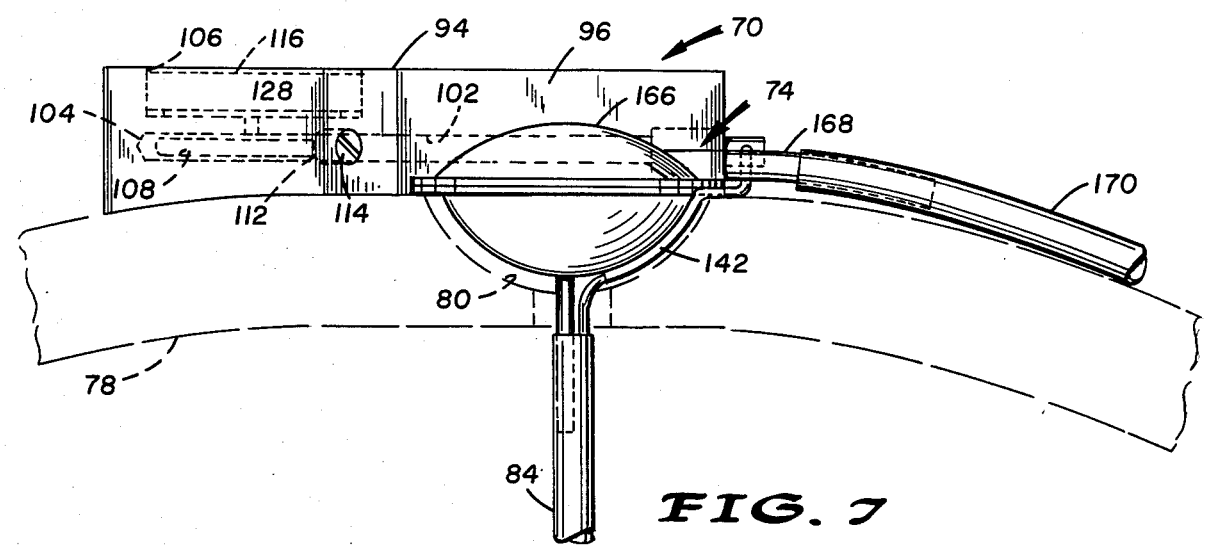
FIG. 7 is an enlarged side cross sectional view of the embodiment of FIG. 6.

Referring to FIGS. 7, 8, and 9, the pressure sensor 70, which is shown implanted in FIG. 6, is illustrated in detail. The pressure transducer 70 includes a housing plate 94 having a contoured depression 96 which is contoured to conform substantially to the outer diameter of the flushing valve 74. A pair of suturing eyelets 98 and 100 are formed in the housing plate 94 to permit suturing thereof to the cranial periosteum. Certainly, however, alternate provisions can be made for fixing the housing plate 94 in position.

A metering channel 102 is formed in the housing plate 94. An end 104 of the metering channel 102 opens into a bellows recess 106 through a bellows channel 108, both disposed in the housing plate 94. The housing plate 94 can be formed from a solid block of Teflon with the metering channel 102 and bellows channel 108 being drilled therein. As a result, a portion 110 of the bellows channel 108 will be a remnant of this manufacturing technique and serves no useful purpose. It therefore can be sealed off with a seal 112 and a threaded closure plug 114 or the like. A diameter of 1.2 millimeters has proven to be satisfactory for the metering channel 102 although other diameters can be employed. A plurality of radiopaque markers 158 which are spaced equidistantly along the longitudinal axis of the metering channel 102 are disposed in the housing plate 94.

The bellows recess 106 accommodates a closed ended bellows assembly 116 which includes a bellows plate 118 and a bellows member 120. The closed end bellows assembly 116, when assembled, has the bellows member 120 mounted to the bellows plate 118, an hermetic seal being made and a chamber being formed therebetween. A plurality of mounting apertures 122 are disposed in the bellows plate 118 and are positioned to align with a plurality of mounting apertures 124 disposed in the housing plate 94. A fluid passage 126 is disposed through the bellows plate 118 and communicates with the interior chamber of the bellows assembly 116. The fluid passage 126 aligns with an opening 128 disposed in the housing plate 94 when the closed ended bellows assembly 116 is mounted within the bellows recess 106. The closed ended bellows assembly is secured within the bellows recess 106 by a plurality of screws 130, one of which is illustrated, each of which passes through one of the mounting apertures 124 of the housing plate 94 and threadably engages one of the mounting apertures 122 disposed in the bellows plate 118.

When the closed ended bellows assembly 116 is in position within the bellows recess 106, the interior of the assembly 116 is in communication with the bellows channel 108 by virtue of the fluid passages 126 and opening 128. The bellows plate 118 seals tightly against the housing plate 94 so that the interior chamber of the closed ended bellows assembly 116 serves to enclose the end 104 of the metering channel 102.

The closed ended bellows assembly 116 is dimensioned so that its height, when assembled, is less than the depth of the bellows recess 106. As a result, the bellows member 120 is not subjected to tissue pressure from the scalp 82 when the pressure sensor 70 is operably positioned as illustrated in FIG. 6. However, the closed ended bellows assembly 116 is subjected to atmospheric pressure through the scalp 82 so that the sensor can operate in a differential mode.

The end 132 of the metering channel 102 provides a plurality of threads 134 for affixing of an elbow fitting 136 to the housing plate 94. The elbow fitting 136 is secured in position by a threaded compression fitting 138 which threadably engages threads 134 and a seal 140. The elbow fitting 136 is connected to one of the lumens of the double lumen tube 84 as hereinafter described by a section of tubing 142. The section of tubing 142 can be integrally formed with the double lumen tube 84 or can be separately manufactured and joined using known mechanical expedients. The tubing 142 passes underneath the flushing valve 174 and through the aperture 80 as illustrated in FIG. 7. With reference to FIG. 10, the double lumen tube 84 is illustrated therein. The double lumen tube includes first and econd discrete lumens 144 and 146. The first lumen 144 provides a passage for the ventricular shunt 72 and opens into the CSF 92 through an opening 148 disposed through the wall of the double lumen tube 84 as illustrated in FIG. 6. The first lumen 144 is connected to the input tube 149 of the ventricular shunt 72 as illustrated in FIG. 7. The first lumen 144 is entirely discrete in relation to the second lumen 146, these lumens not being in communication.

A flexible tambour 150 is disposed about the double lumen tube 84, the interior thereof being in communication with the second lumen 146 through an opening 152 disposed in the double lumen tube 84. The section of tubing 142 is also in communication with the second lumen 146 thereof connecting the metering channel 102 thereto. The flexible tambour 150, which is preferably constructed of silastic material, has a side wall including a plurality of undulations 154 to enhance the reaction of a flexible tambour 150 to pressure. This enhancement is a result of the flexible tambour's walls requiring only the bending thereof when subjected to increased pressures. In contrast, if a circular cross-section is employed, the configuration is inherently more resistive to collapsing since compression of the material in its own plane must be effected rather than the bending thereof. In order to check the position of the double lumen tube 84 when implanted, a radiopaque marker 156 is provided in the end thereof as illustrated in FIG. 6. In addition, the lumens 144 and 146 are plugged at this location.

When the pressure sensor 70 is prepared for use, the bellows assembly 116, the bellows channel 108, and a portion of the metering channel 102 adjacent to the end 104 thereof are filled with a radiopaque liquid 160 such as Pantopaque. The balance of the metering channel 102, the elbow fitting 136, the section of tubing 142, and the second lumen 146 as well as the flexible tambour 150 are filled with a saline solution 162, immiscible with the radiopaque liquid 160. A meniscus or interface 164 is thereby formed between the radiopaque liquid 160 and the saline 162 as illustrated in FIG. 8. This interface 164 shifts along the metering channel 102 as the pressure sensor 70 is subjected to varying pressure. The positional relationship of the interface 164 to the radiopaque markers 158 therefore gives an indication of changes in pressure measured by the sensors 70.

As pressure in the ventricular 90 increases, the flexible tambour 150 collapses forcing the saline solution 162 thereout. This causes a shift of the saline solution in the metering channel 102 thereby shifting the interface 164 and the radiopaque liquid 160. The result of this is to expand the bellows member 120 to accommodate shifting of the radiopaque liquid 160. If the head 76 is X-rayed, the shift of the interface 164 relative to the radiopaque markers 158 can be observed so that the change in pressure in the ventricle 90 will be known. If the markers 158 are calibrated, this shift can be read out directly in pressure on the X-ray film.

If a decrease in pressure occurs within the ventricle 90, the tambour 150 will relax and the interface 164 will shift in a direction opposite that which occurs with an increase in pressure.

The sensors 22 and 70, are of the differential type since these devices are sensitive to pressure both at their tambours, 40 and 150 respectively, and their closed ended bellows assemblies 58 and 116. The tambours 40 and 150 are subjected to ventricular pressure and the bellows assemblies 58 and 116 are subjected to atmospheric pressure through the scalp of the subject. As a result, changes in pressure observed by the sensors 22 and 70 will automatically be corrected for changes in atmospheric pressure to give a corrected pressure reading.

When an increase in ventricular pressure is observed, it can be relieved in a customary manner by venting of the CSF 92 through the ventricular shunt 72. By pushing on the flexible upper portion 166 of the flushing valve 74, CSF 92 is drawn up through the first lumen 144 of the double lumen tube 84, is drawn through the input tube 149 of the flushing valve 74 and is discharged out a discharge tube 168 provided by the flushing valve 74. A section of tubing 170 is fixedly secured to the discharge tube 168 of the flushing valve 74 and is routed in a customary manner to an appropriate area of the body for discharge of the CSF 92.

The use of flushing valves and ventricular shunts is quite well known. Through use of the configuration of the present invention shown in FIGS. 6 through 10, by using the presently refined procedure of implanting these apparatuses, simultaneously, a pressure sensor of the described character can also be implanted. This permits an integrated and compact procedure which does not suffer from unknown medical complications since no new technique is required. Of course, if a flushing valve is employed of a different configuration than the one illustrated, the housing of the pressure sensor can be suitably modified in shape to conform closely to this alternately configured flushing valve.

It should be apparent that many other mechanical configurations can be utilized to achieve the same results as hereinbefore set forth within the principles of the present invention as explained in conjunction with FIG. 1 and that these teachings can be employed in pressure sensors for parts of a human body other than the head.

It also will be understood that various changes in the details, materials, arrangements of parts and operational conditions which have been herein described and illustrated in order to explain the nature of the invention may be made by those skilled in the art within the principles and scope of the present invention.

Having thus set forth the nature of the invention what is claimed is:

1. A biological pressure sensor for implantation at selected site within the body of a human subject comprising:

a housing plate, said plate having disposed therein a bellows recess and an elongated metering channel opening on one end thereof into said recess, said housing plate adapted to be fixedly secured to biological tissue;

a closed ended bellows for mounting in said bellows recess, the interior of said bellows communicating through an aperture disposed in a wall thereof to said bellows recess and therefore to the interior of said one end of said metering channel;

a pressure tube fixedly secured on one end thereof to the other end of said metering channel, said tube communicating with the interior of said metering channel;

a flexible tambour operably connected to the other end of said pressure tube, said flexible tambour for positioning at said selected site, the pressure of which is to be measured;

an X-ray detectable liquid disposed in said bellows and the interior of the adjacent portion of said metering channel; and a second liquid immiscible with said X-ray detectable liquid disposed in said tambour, the interior of said pressure tube, and the balance of the interior of said metering channel not filled with said X-ray detectable liquid, said X-ray detectable liquid being relatively radiopaque in comparison to said second liquid, the interface between said liquids moving along the length of said metering channel in proportion to increases and decreases of said pressure.

2. A biological pressure sensor in accordance with claim 1, further comprising a plurality of X-ray detectable radiopaque markers disposed in said housing plate along the length of said metering channel, said markers serving as points of reference to which movement of said interface can be compared.

3. An implantable ventricular pressure sensor and shunt comprising:

a ventricular flushing valve;

a double lumen tube having first and second discrete lumens, said tube for insertion into the ventricle of a subject, said first lumen being in communication at one end thereof with the cerebral spinal fluid in said ventricle and in communication at the other end thereof with the input of said ventricular flushing valve;

a flexible tambour in communication with said second lumen, said tambour being disposed in said ventricle for sensing pressure changes in said cerebrospinal fluid;

an elongated metering channel in communication on one end thereof with said second lumen;

variable volume means in communication with the other end of said metering channel;

fluid means disposed in said flexible tambour, the interior of said metering channel, and the interior of said variable volume means; and moveable X-ray detectable radiopaque means disposed within said metering channel, said radiopaque means moving along the length of said channel in proportion to increases and decreases of said pressure manifested as relative changes of volume between said tambour and said variable volume means and the shifting of said fluid means therebetween.

4. An implantable verticular pressure sensor and shunt in accordance with claim 3 wherein said fluid means and said moveable X-ray detectable radiopaque means comprise a radiopaque fluid disposed in the interior of said variable volume means and in an adjacent interior portion of said metering channel connected thereto, and a second fluid, the balance of the interior of said metering channel and said flexible tambour being filled by said second fluid.

5. An implantable ventricular pressure sensor and shunt in accordance with claim 4, wherein said second fluid comprises a liquid immiscible with said radiopaque liquid, the interface between said fluid and said radiopaque liquid moving along the length of said metering channel in proportion to increases and decreases of said pressure.

6. An implantable ventricular pressure sensor and shunt in accordance with claim 5, wherein said movable volume means comprises a closed ended bellows.

7. An implantable ventricular pressure sensor and shunt in accordance with claim 6, further comprising a housing plate, said metering channel being disposed in said housing plate, said housing plate adapted to be fixedly secured to the cranium of said subject for disposition entirely beneath the scalp of said subject, said housing plate having a bellows recess disposed therein, said bellows being operably mounted within said bellows recesses so as to preclude tissue pressure of said scalp from interfering with movement of said bellows.

8. An implantable ventricular pressure sensor and shunt in accordance with claim 7, wherein said housing plate is contoured so a portion thereof is formed with a circular concave recess to receive a circular convex contour of said ventricular flushing valve.

9. An implantable ventricular pressure sensor and shunt in accordance with claim 7, wherein said housing plate comprises Teflon.

10. An implantable ventricular pressure sensor and shunt in accordance with claim 9, further comprising a plurality of X-ray detectable radiopaque markers disposed in said housing plate along the length of said metering channel, said markers serving as points of reference to which movement of said interface can be compared.

* * * * *